United States Patent [19]

Seigel et al.

[11] 4,365,153

[45] Dec. 21, 1982

[54] DETECTION OF CERTAIN MINERALS OF ZINC, TUNGSTEN, FLUORINE, MOLYBDENUM, MERCURY AND OTHER METALS USING PHOTOLUMINESCENCE

[75] Inventors: Harold O. Seigel, Don Mills; John C. Robbins, Alliston, both of Canada

[73] Assignee: Scintrex Limited, Alliston, Canada

[21] Appl. No.: 159,792

[22] Filed: Jun. 16, 1980

[30] Foreign Application Priority Data

Jun. 25, 1979 [GB] United Kingdom ............... 7922000

[51] Int. Cl.$^3$ ............................................. G01V 5/00
[52] U.S. Cl. ................................. 250/253; 250/459.1; 250/461.1
[58] Field of Search .................... 250/253, 461 R, 364, 250/365

[56] References Cited

U.S. PATENT DOCUMENTS

| Re. 25,320 | 1/1963 | Lewis et al. ............ 250/461 R |
| 2,987,620 | 6/1961 | Lewis et al. ............ 250/461 R |
| 3,043,908 | 7/1962 | Madsen .................... 250/253 |
| 3,663,814 | 5/1972 | Madsen .................... 250/253 |
| 3,666,945 | 5/1972 | Frungel et al. .......... 250/365 |
| 3,736,428 | 5/1973 | Monroe .................... 250/461 R |
| 3,886,363 | 5/1975 | Ohnishi et al. .......... 250/365 |
| 4,236,071 | 11/1980 | Chimenti ................ 250/253 |

FOREIGN PATENT DOCUMENTS

| 1064726 | 5/1977 | Canada . |
| 2438888 | 2/1976 | Fed. Rep. of Germany . |
| 2537098 | 3/1976 | Fed. Rep. of Germany . |

OTHER PUBLICATIONS

Bennett, Instrument to Measure Fluorescence Lifetimes in the Millimicrosecond Region, pp. 1275-1279.
Benson et al., Concentration and Temperature Quenching of the Excited State of the Uranyl Ion in Aqueous Solution by Laser Flash Photolysis, pp. 195-197.
Yokoyama, Election Transfer Mechanism in Quenching of Uranyl Luminescence by Halide Ions, pp. 1329-1333.

*Primary Examiner*—Davis L. Willis
*Attorney, Agent, or Firm*—Sim & McBurney

[57] ABSTRACT

We have discovered that certain photoluminescent minerals of zinc, fluorine, tungsten, molybdenum, mercury and other elements which may naturally occur at the surface of the earth can be selectively detected in the presence of most other photoluminescent minerals and organic materials which are likely to occur at the earth's surface. The basis of selective detection is the discovery that the lifetimes of photoluminescent emission of materials in the latter class are much shorter than the lifetimes of photoluminescent emission of materials in the former class. This invention utilizes this discovery in the detection of minerals of uranium, zinc, lead, fluorine, tungsten, molybdenum, mercury and other elements. In one embodiment of the invention, using a laser or other short duration source of optical excitation, measurements of the photoluminescent response of the earth are made at times sufficiently long for the photoluminescence of other common and unwanted sources to have substantially decayed, thereby selectively detecting and identifying certain minerals of potential economic interest. In another embodiment a source of light is modulated at a predetermined frequency and the photoluminescent response of the earth which is out-of-phase with the source is measured. In a third embodiment this source of light may be incident solar radiation after passage through a suitable modulator.

26 Claims, 14 Drawing Figures

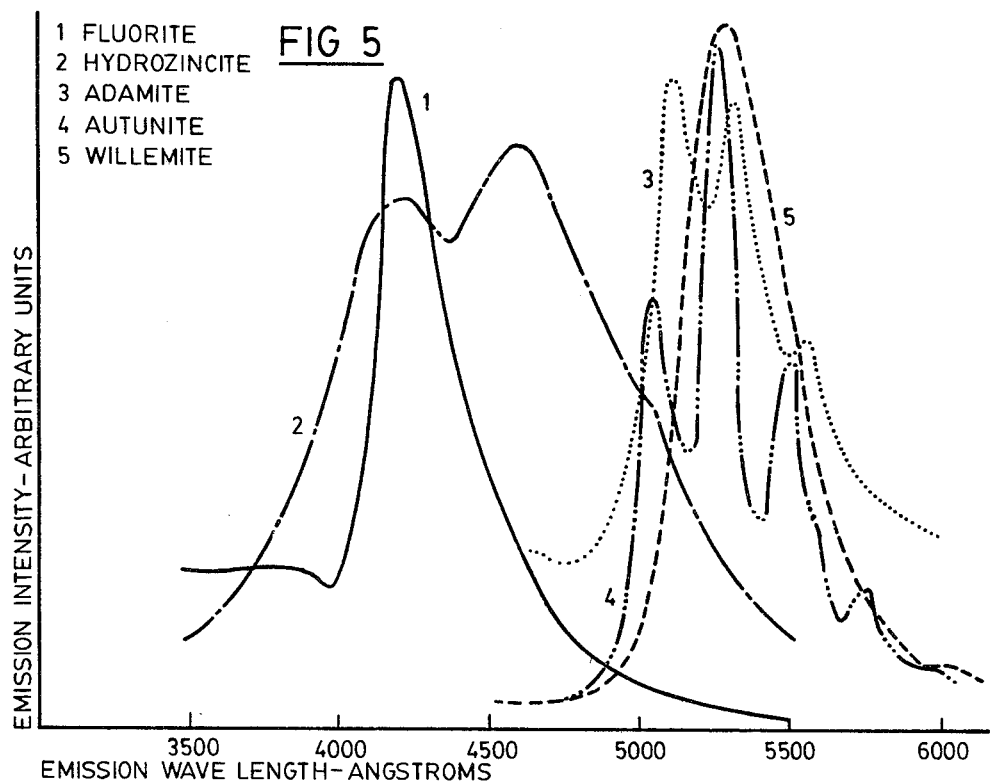
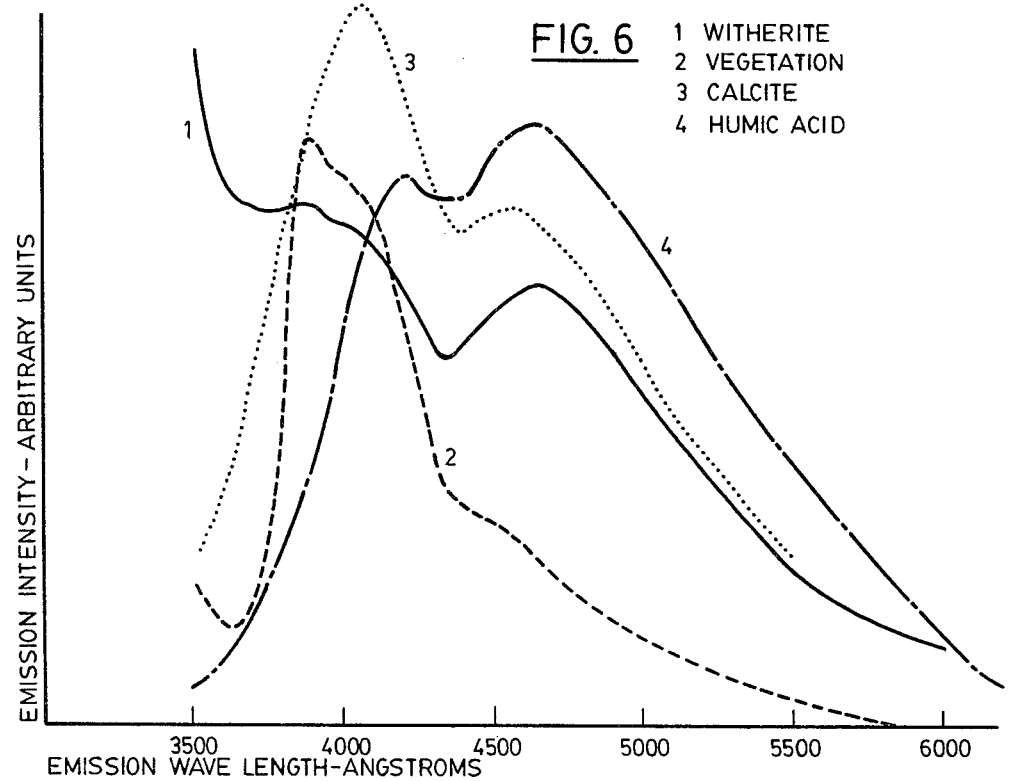

DETECTION OF CERTAIN MINERALS OF ZINC, TUNGSTEN, FLUORINE, MOLYBDENUM, MERCURY AND OTHER METALS USING PHOTOLUMINESCENCE

Photoluminescence is that property of certain substances whereby they emit light when irradiated by incident light of suitable wavelength, usually ultraviolet. There are two types of photoluminescence, normally designated by the terms fluorescence and phosphorescence. It is sometimes difficult to determine which of these types of luminescence applies in a specific case, but the following distinction has been used in the geological literature. If the radiated light exists only during or for very short times (undefined) after the duration of the incident light, the substance is termed fluorescent. If the radiated light measurably persists for a much longer time (perceptible to the eye), that is, usually one second or longer after the interruption of the incident light, the substance is termed phosphorescent (e.g., see Dana, "A Textbook of Mineralogy", John Wiley & Sons, N.Y.). To our knowledge, so far as the earth science literature concerned with measurement of the luminescence of geologic materials reveals, the distinction between these two types of luminescence has been made only with the naked eye until the investigations by the inventors of this invention.

Under constant excitation conditions the fluorescent emission of a given mineral also will be constant, there being an equilibrium developed between the various absorption and emission processes. If, however, the incident radiation is interrupted suddenly, the fluorescence will decay over a finite period of time.

The intensity of the photoluminescent emission from a sample after the interruption of the incident radiation usually can be expressed as a function of time, as follows:

$$I_t = I_o e^{-t/\tau} \quad (1)$$

where $I_t$ is the intensity at a time t after the incident radiation is interrupted; $I_o$ is the intensity at the time t=o; and $\tau$ is a constant for a specific emission, usually being known as the "lifetime" of the photoluminescence.

The geological literature reveals the fact that many naturally occurring minerals are known to be fluorescent under short wave excitation, commonly ultraviolet radiation from a mercury lamp. Among the most common of these are adamite, anglesite, autunite, apatite, barite, calcite, cerussite, fluorite, gypsum, halite, nepheline, quartz, scheelite, willemite and zircon. A few of these minerals also are known to be phosphorescent, although rarely in all specimens, suggesting that conventional phosphorescence, as defined above, is more a function of impurities or activators in the mineral structure than it is a fundamental property of the mineral itself.

The observation of the phosphorescence of a mineral can be made by irradiating a specimen of the mineral with a UV (mercury) lamp in a dark room, extinguishing the lamp and visually observing the luminescence emitted by the specimen for a few seconds. Those naturally occurring minerals which are designated "phosphorescent" by the current geologic literature have lifetimes of photoluminescence which are of the order of seconds in duration.

Minerals that show similar fluorescent intensities under continuous excitation may show very different temporal characteristics under pulsed excitation. Two minerals such as willemite and autunite may exhibit similar intense green fluorescence under continuous excitation but under pulsed conditions the mineral with the shorter lifetime (autunite) will fluoresce during its period of emission very much more strongly than the mineral with the longer lifetime. The integrated values of the intensity function given by equation (1) will be thus more or less equal for the two minerals giving rise to the visual impression that the average intensity of fluorescence is indeed equal.

The characteristic strong fluorescence of certain common ore minerals, for example, scheelite (ore of tungsten) and fluorite (ore of fluorine), when excited by an ultraviolet lamp (black light) has been extensively used in prospecting for these ores ("Ultraviolet Guide to Minerals" by S. Gleason, published by Van Nostrand, 1960). The UV lamp is shone on the rock samples in a darkened room in search of the characteristic colored fluorescent emission of the ores in question. Some attempts, including successful discoveries, also have been made using a UV lamp as a prospecting tool at night, but these uses are rare, being impractical in areas of rough ground or for rapid coverage of large areas. A further and more fundamental problem encountered in the use of fluorescence as a general prospecting tool is the very broad range of luminescent substances, organic and inorganic, which may occur at the earth'surface. Their fluorescent emission spectra are broad and usually overlapping, so that a clear resolution of the fluorescent emission of one particular mineral from the broadly fluorescent background (noise) from other fluorescent sources is not normally obtainable.

The use of fluorescent techniques in mineral exploration has been limited by:

(1) the low intensities of fluorescent emission, and the corresponding need for night time operation, or the use of inconvenient hoods or dark rooms; and (2) the apparent randomness and lack of specificity of fluorescent methods. Minerals from one locality may behave quite differently from similar minerals from another locality; conversely, the fluorescent responses of quite different minerals sometimes appear very similar. While a geologist experienced in fluorescent techniques undoubtedly would identify such minerals by other characteristics, the ambiguity of an instrumental determination would preclude quantitative measurements. The power of instrumental methods are after all only useful if the output of the instrument can be realized as a definitive, quantitative indication of the presence of the minerals sought. Particularly in remote sensing where the distance between instrument and mineral surface does not allow independent interpretation by the geologist, his dependence on the instrument reading is complete.

The fluorescent properties of a few minerals are, however, quite consistent from locality to locality, deposit to deposit. Amongst these are important economic minerals of tungsten, molybdenum, zinc and uranium, which include scheelite, powellite, hydrozincite and the many uranyl minerals respectively. While it seems clear that the fluorescence of these minerals, excepting the uranyl group, is due to the incorporation of trace amounts of "activator" ions, the presence of these ions seems sufficiently consistent that, with minor variations, fluorescence of scheelite, powellite and hydrozincite from many localities is essentially similar. The spectral and temporal characteristics of fluorescence have been presented for scheelite (calcium tungstate) in "Luminescence of Calcium Tungstate Crystals" by J. J. Treadaway and R. C. Powell, J. Chem. Phys. 61, pages 4003 to 4011, 1974, and for the uranyl minerals by many authors, e.g., "Temperature Dependance of Fluorescence Decay of Uranyl Salts" by D. D. Pant, H. C. Pant and D. N. Pande, Indian J. Pure Appl. Phys., Vol. 6, pages 122–125, 1968. Similar results for these minerals and for powellite and hydrozincite (hitherto unpublished) now have been determined in our laboratory. Table 1 presents the luminescent properties of some of the minerals of economic interest with which this invention is concerned.

In a remote sensing method operating under daylight conditions, the principal limitation to detection of the faint fluorescent emission is imposed by (a) the effects of solar radiation reflected from the mineral surfaces under investigation, and (b) the presence of other unwanted fluorescent components in that surface. The steady components of the solar radiation can be blocked by AC coupling, but any fast-changing variations in light reflected from the surfaces and the electronic noise intrinsic to the photocurrent generated by the solar radiation will determine the minimum detectable change in intensity that can be reliably ascribed to fluorescence.

When a pulsed laser is used as excitation source, for a given laser power, the detectability of apparently equally brightly fluorescent minerals depends on their fluorescence lifetimes. In the example given earlier, autunite would be more readily detected than willemite, since the fluorescent intensity of autunite over its shorter period of emission is stronger relative to that of willemite. It is therefore stronger relative to the reflected solar radiation, and hence more easily resolved. (The enhancement is reduced slightly by the increased bandwidth needed to "capture" the shorter-lived fluorescence signal).

We have found experimentally that, with UV laser powers of the order of 50 millijoule, surface exposures of less than 1% of scheelite and hydrozincite and less than 10% autunite can be detected at distances of at least 80–90 meters under daylight conditions. The detectability of fluorescent intensity often may be improved by increasing laser powers. If, however, the second limitation to sensitivity, the presence of other unwanted fluorescent species is dominant, no advantage will be gained. Suppose, for example, that the expected occurrence of the desired fluorescent mineral is, say, 1% by area of the host rock. Even if the host rock exhibits an intrinsic fluorescent yield that is only 1% of that of the desired mineral, the response of the latter will be essentially masked over all ranges of excitation intensity. Under continuous excitation conditions, this often may be the case, since there are so many fluorescent minerals that give rise to the usually diffuse and weak blue fluorescence of many rock surfaces.

In the literature it has been shown that, whereas rock-forming minerals, if totally pure, are usually nonfluorescent, the presence of certain activator ions dispersed through the mineral gives rise to predictable fluorescence response. Activator ions may be present as a single species in a crystal or, as has been shown in a number of examples, the simultaneous presence of two species is required to generate a specific fluorescence emission. From the literature we find that the lifetimes of fluorescence of compounds with these activator ions can be expected to range from 10–2000 microseconds, (see "Fluorescence Decay of Rare-Earth Ions in Crystals" by G. E. Barasch and G. H. Dieke, J. Chem. Phys. 43, pp. 988–994, 1965). In the case of sodic feldspars lifetimes from 5–10 microseconds were observed (see "Application of Ultraviolet Reflectance and Stimulated Luminescence to the Remote Detection of Natural Materials" by W. R. Hemphill, Interagency Report, NASA-121, 1968). Since these values would fall in the range of lifetimes exhibited by the minerals of interest their presence in a rock would seriously limit detectability. It also should be noted that the emission spectra of some common rock types have been presented by R. M. Measures, W. R. Houston, D. G. Stephenson in "Laser-Induced Fluorescence Decay Spectra—A New Form of Environmental Signature", Optical Engineering Vol. 13, p.494–501 1974.

In contrast to the data available in the literature, we have found that the fluorescent lifetimes of the common rock types derived from areas devoid of mineral deposits, under the conditions of short pulse length UV excitation as used in the present application, are in fact extremely short. Visible fluorescence from most rock types was readily apparent even under daylight interior lighting conditions but the lifetime of fluorescence was instrumentally determined to be almost invariably less than 0.2 microsecond. Table 2 lists the colors and lifetimes of fluorescence of 58 common rocks and minerals recently tested. Fluorescence with such a short lifetime will have largely decayed by the time the corresponding measurements are made on the minerals of interest, which have fluorescent lifetimes in excess of 1.1 microseconds. It can be seen that, therefore, contrary to the literature, the presence of these background fluorescing materials in so many common rock types will not be a significant factor in limiting detectability of the presence of the selected minerals referred to above.

Those common minerals known to occasionally display phosphorescence (within the usual geologic meaning of the term), such as calcite, gypsum, kunzite, sodalite etc., may have photoluminescent lifetimes of the order of seconds. Their luminescence is impurity activated, often by manganese, lead or rare earth impurities. Their intensities are always low, inversely proportional to their lifetimes. If we concern ourselves with measurements of luminescence during the 1 to 50 microsecond lifetimes of the minerals of interest to this invention, as in Table 1, for example, then we may expect little influence from most "phosphorescent" minerals.

In accordance with this invention there are provided methods and apparatus whereby certain common non-uranyl minerals of zinc, fluorine, tungsten, molybdenum, mercury and other elements which may occur naturally near the surface of the earth may be detected through their special, distinctive, luminescent properties, even in the presence of the usual background fluorescent noise from vegetation and common mineral species. Means are provided whereby such detection may take place even under conditions of relatively high ambient light e.g., daylight.

In accordance with one aspect of this invention there is provided a method of selectively rejecting the fluorescent response of the abundant photoluminescent rocks and substances which may occur at the surface of the earth, while detecting the fluorescent response of a non-uranyl mineral of economic significance selected from the group consisting of minerals of zinc, fluorine, tungsten, molybdenum, mercury and other elements having lifetimes of photoluminescence between 1 and 50 microseconds through consideration of their differences in photoluminescent lifetimes; said method comprising the steps of directing at the ground electromagnetic radiation having an intensity that varies with time and of a wavelength that causes photoluminescence of said mineral; selectively detecting photoluminescent emission from said mineral in a wavelength region which is characteristic of emission of photoluminescence of said mineral; and selectively detecting the presence of said mineral by measuring the time varying detected photoluminescence excited by said radiation and due to minerals selected from said group having lifetimes of photoluminescence between 1 and 50 microseconds.

According to another aspect of this invention there is provided apparatus for selectively rejecting the fluorescent response of the abundant photoluminescent rocks and substances which may occur at the surface of the earth, while detecting the fluorescent response of a non-uranyl mineral of economic significance selected from the group consisting of minerals of zinc, fluorine, tungsten, molybdenum, mercury and other elements having a lifetime of photoluminescence between 1 and 50 microseconds through consideration of their differences in photoluminescent lifetimes; said apparatus comprising a source of electromagnetic radiation having a wavelength that causes photoluminescence of said mineral; means for modulating said source with a fundamental frequency of modulation between about 3 kHz and about 160 kHz; means for selectively detecting photoluminescent emission from said mineral in a wavelength region which is characteristic of emission of photoluminescence of said mineral; and means for measuring the phase lag of the detected photoluminescent emission from said mineral relative to the phase of said modulation of said electromagnetic radiation.

This invention will be better understood from the following detailed description, taken in conjunction with the appended drawings, in which:

FIG. 5 shows the luminescent emission spectra of fluorite, hydrozincite, adamite, autunite and willemite;

FIG. 6 shows the emission spectra of witherite, calcite, humic acid and vegetation;

Figure 1:
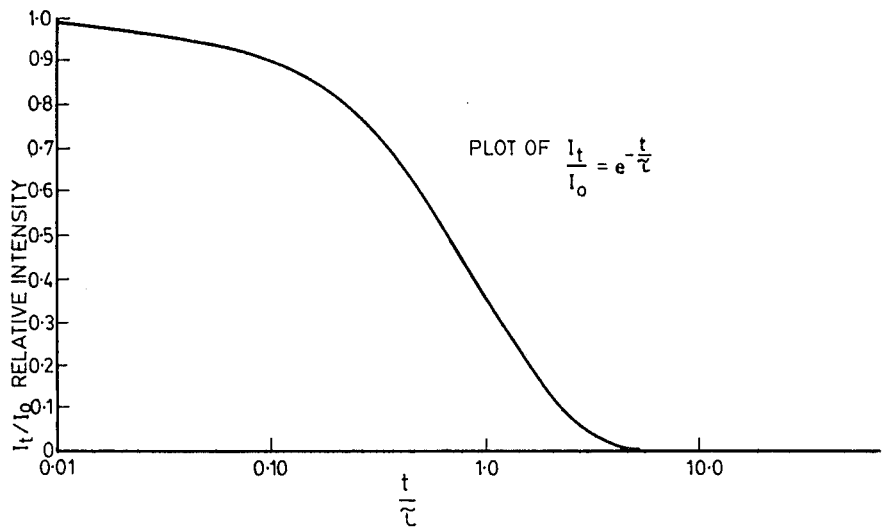
FIG. 1 is a plot of equation (1) on a logarithmic time basis.
Figure 2:
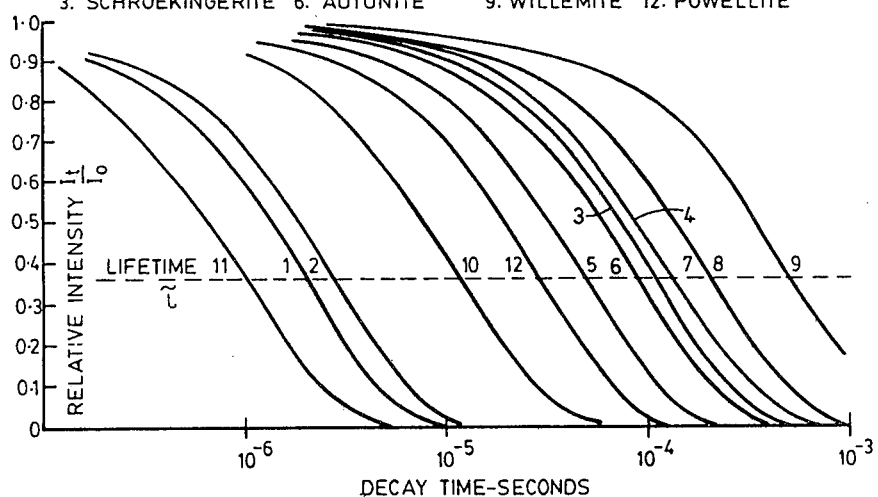
FIG. 2 shows the decay with time after the interruption of the incident light of the photoluminescence from fluorite, zippeite, schroekingerite, andersonite, adamite, autunite, anglesite, cerussite, willemite, scheelite, hydrozincite and powellite.

FIG. 2 shows the photoluminescent decay of natural crystals of adamite, andersonite, anglesite, autunite, cerussite, fluorite, powellite, schroekingerite, willemite, zippeite and scheelite. The excitation source employed in obtaining the results plotted in this Figure was a nitrogen laser, with radiation at 337 nm and a pulse duration of 4 nanoseconds, except for scheelite and powellite, for which a KrF laser 248 nm was used. For decay shape comparison the initial luminescence from each sample has been normalized to the same value. The lifetime $\tau$ for each of these decays is determined by the time at which it decays to 0.36 of its initial value. The significance of certain of these minerals is that they are common secondary minerals of uranium, lead and zinc which may be expected to occur near the surface of the earth. They are usually the product of the breakdown by weathering of primary minerals of these metals—for example, pitchblende, galena, and sphalerite (through oxidation in the near surface environment). Fluorite is a primary mineral (and ore) of fluorine and scheelite and powellite are primary minerals (and ores) of tungsten and molybdenum which may occur in surface outcrops of rocks containing these minerals.

An examination of these curves shows that the lifetime of photoluminescence of these minerals is long or even very long in comparison with that normally associated with fluorescence of common rock forming minerals. Lifetimes observed range from 1 microsecond to 500 microseconds.

Figure 3:
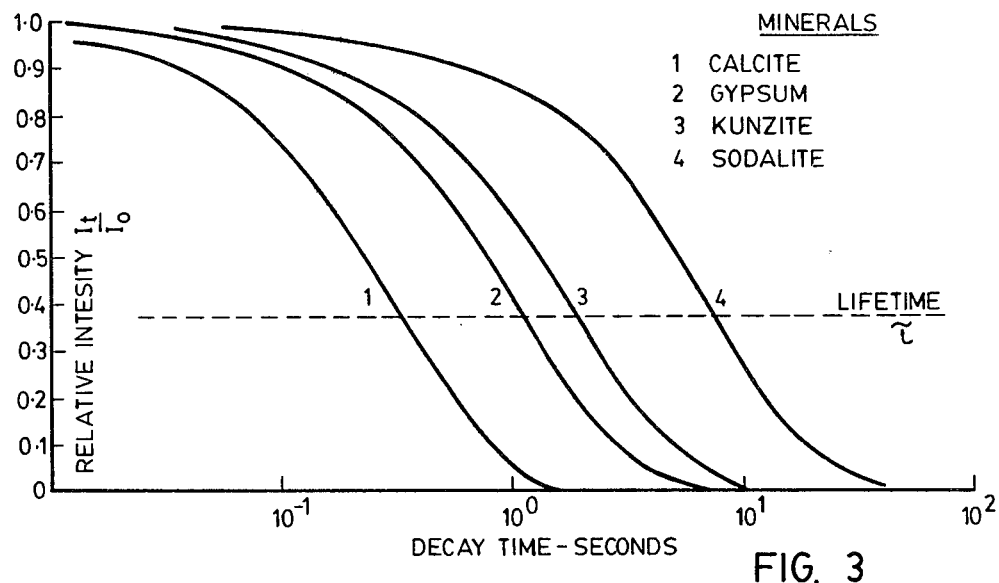
FIG. 3 shows the time decay of photoluminescence from some common "phosphorescent" minerals, namely calcite, gypsum, kunzite and sodalite.

FIG. 3 shows the decay of photoluminescence of selected specimens of calcite ($CaCO_3$), gypsum ($CaSO_4.2H_2O$), kunzite ($LiAlSi_2O_6$) and sodalite ($Na_4Al_3Si_3O_{12}Cl$) which are "phosphorescent" in accord with normal geologic terminology, i.e., with lifetimes in excess of 0.1 seconds and mainly in excess of 1 second. These lifetimes are, therefore, as much as three orders of magnitude larger than those of the minerals shown in FIG. 2 and which are of interest to this invention. The peak intensity ($I_o$) for such long lived luminescence is usually very small, being inversely proportional to their lifetime. In addition, such phosphorescent varieties are rather rare, their phosphorescence being activated by impurities such as rare earths, manganese and lead in their crystal structure. As a result of these three factors, we will observe little influence from such phosphorescent minerals, providing that we make luminescent measurements within the lifetimes of the minerals of interest to this invention, viz. 1–50 microseconds.

Figure 4:
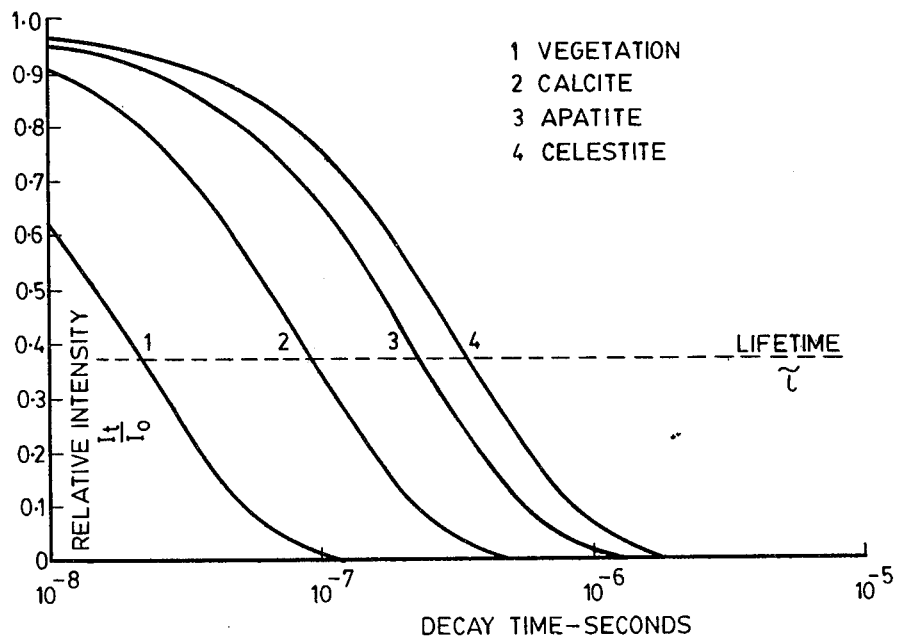
FIG. 4 shows the time decay of photoluminescence from some common, normally economically unimportant, fluorescent sources.

FIG. 4 shows the decay of photoluminescence for some other common minerals and organic materials which are also likely to occur at the surface of the earth. It is apparent that the photoluminescent lifetimes for these substances are much shorter, not exceeding 1 microsecond, which we have found to be typical for most organic and non-economic mineral fluorescers at the surface of the earth.

FIG. 5 shows the photoluminescence spectra of various minerals noted in the Figure, while FIG. 6 shows the equivalent spectra for various fluorescent substances noted in the Figure. From the breadth and spread of the spectral peaks of FIG. 6, it is clear that spectral analysis alone could not provide a reliable means of differentiating photoluminescence from minerals of FIG. 5 and the substances of FIG. 6.

Our discovery is the unexpected fact that the vast bulk of fluorescent minerals that have hitherto limited the practical application of fluorescence as an exploration tool, have lifetimes of photoluminescence which are less than one microsecond. This allows us to selectively detect certain important minerals of economic interest which have photoluminescent lifetimes of between 1 microsecond and 50 microseconds, even in the presence of the much more abundant, non-economic fluorescing minerals.

Figure 7:
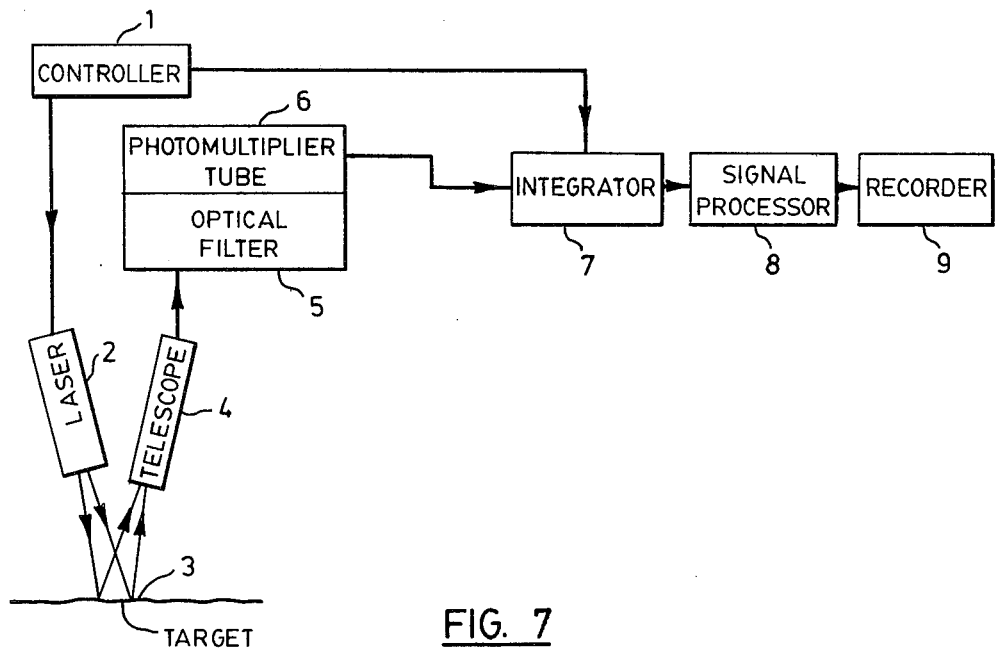
FIG. 7 is a block diagram of a typical single channel equipment that may be used in practising the instant invention.

FIG. 7 illustrates one embodiment of this invention as might be applied in the field either on the ground or using an aircraft as transport. A pulsed UV laser 2 driven by an electronic controller 1 beams a short (for example, 5 to 10 ns) pulse of light towards a ground target 3. The pulse duration should preferably be shorter than the lifetime of photoluminescence of the mineral species of interest in order not to be wasteful of energy. The laser may be a nitrogen laser (relatively longwave 337 nm) or an excimer laser (relatively short wavelength, e.g. 250 nm). Other ultraviolet emitting sources than a laser could be used but are not preferred because of their inability to provide short, high energy and directional pulses. A telescope 4 is focused on the same target. The output of the telescope is passed through an optical filter 5 whose passband encompasses the spectral peak of the photoluminescence from the mineral desired (e.g., 450 nm for hydrozincite, etc.). The filtered beam then enters a photomultiplier tube (PMT) 6 which has optimum efficiency in the desired region of the spectrum. The output of PMT 6 is gated by controller 1 into an integrator 7 so that, in effect, the area under one or more segments of the decaying photoluminescence curve are integrated. Different luminescent species can be resolved by the measurement of different segments of the decay curve.

Figure 8:
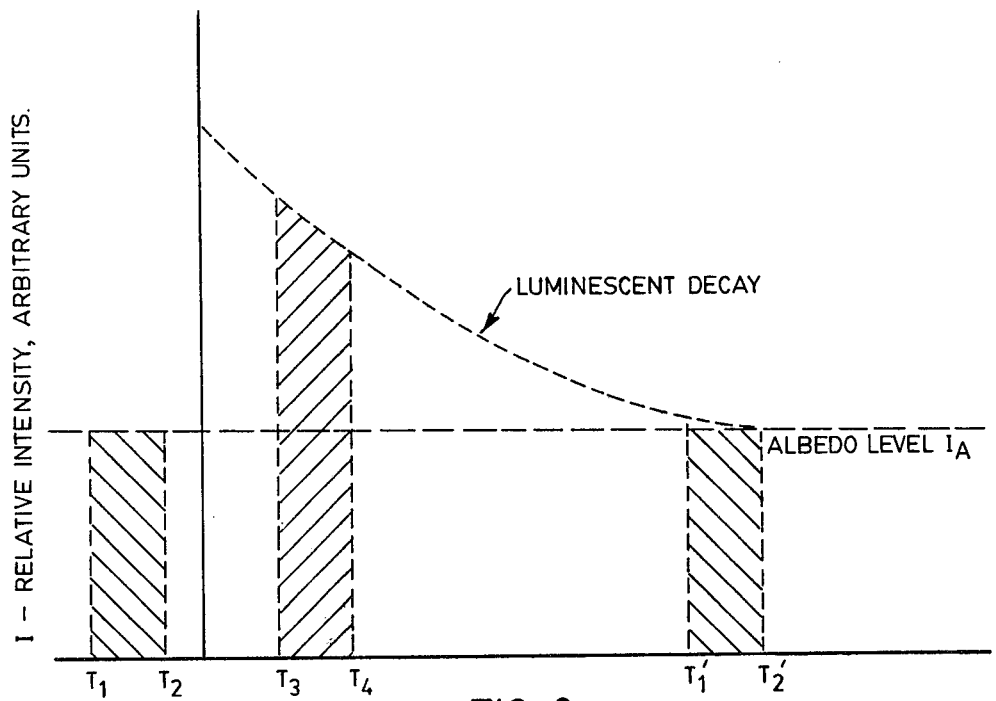
FIG. 8 shows the relative time gating of the light source and the various time resolved detector channels in the apparatus of FIG. 7.

FIG. 8 shows a typical photoluminescent decay curve ($I_t$) and illustrates how measurements are made using the FIG. 7 embodiment of the invention. Firstly, a reference measurement (usually an integration) is made over a time interval T1 to T2 just before the firing of the laser. The purpose of this measurement is to establish the ambient background light level $I_A$ or albedo, in the spectral band of interest. This measurement also corrects for the dark current of the PMT. This measurement will be used to correct the subsequent measurement of the decay of the photoluminescence for this background level in order to resolve the luminescent decay contribution.

A subsequent integration of photoluminescent intensity is made between times T3 and T4, i.e., between 1 and 50 microseconds. The value obtained between times T1 and T2 is subtracted from that between times T3 and T4 in the signal processor 8. The presence of a difference, which will be recorded by recorder 9, may be taken as indicative of the presence of photoluminescent minerals with lifetimes in the desired range. In order to determine the shape of the photoluminescent decay curve one may integrate over a series of time segments, generally contiguous in time. Typically the segment widths increase progressively with increasing time in order to reduce the effect of the short term fluctuations in albedo, PMT and electronic noise. From these multiple measurements the decay curve form may be reconstructed and, for example, the appropriate value of $\tau$ may be determined.

Alternatively, the albedo level may be determined by integration over a time segment T1 and T2 after the pulse, where the delay T1 is long compared with the life-times of interest (e.g., five times greater than the longest expected lifetime of interest).

Providing that the PMT is operating in the linear portion of its range, the effect of the correction for albedo will allow useful single measurements of luminescent intensities which are as low as twice the albedo level fluctuations. Normally the laser is fired repetitively, for example 10 to 100 pulses per second, and the same time segment is integrated for each pulse and stacked, so that the signal-to-noise ratio may be improved, usually by the square root of N, where N is the number of laser pulses integrated. In this event, for 100 pulses (a 1 second measurement), a photoluminescent signal of only 10% of the statistically random albedo noise may be detected. This allows useful detection in full sunlight of the photoluminescent secondary minerals of zinc for example, even at relatively low levels of concentration, e.g., a few hundred parts per million by weight, in the surface environment.

Figure 9:
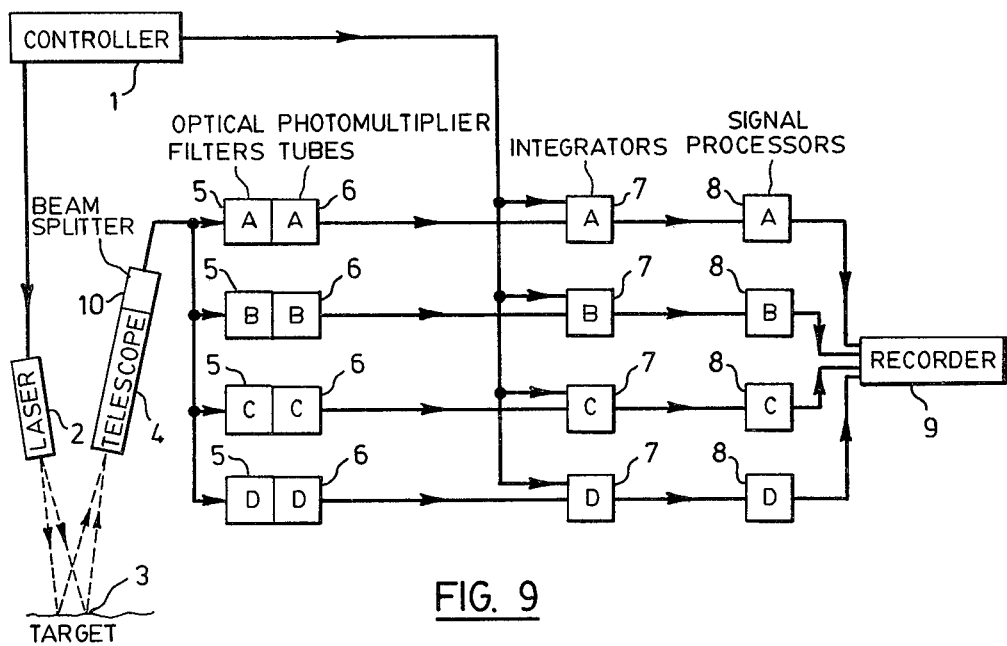
FIG. 9 is a block diagram of typical, multichannel detection equipment which may be used in practising the instant invention.

FIG. 9 is a block diagram of a multispectral embodiment of this invention. In this embodiment the light from telescope 4 passes through a beam splitter 10 and thereafter to a series of channels, each channel having its own filter 5, PMT 6 and operating in the same way as the single spectral channel embodiment of FIG. 7. The number of channels and the filter pass bands are so selected as to cover the total width of the photoluminescent spectrum of those minerals of potential interest. In this manner, through both spectral and time resolution, the photoluminescence from all of these minerals may be measured simultaneously and their presence at the earth's surface approximately established and resolved, one from the other. In this regard, all of the time segments beyond about 1 microsecond after the pulse interruption will be essentially free of any photoluminescent contribution from organic materials and the vast bulk of common geologic luminescence of no geologic interest. At the same time, those luminescent species which are known to be phosphorescent in the classical sense, that is, have lifetimes of the order of seconds or longer, are characteristically of very low luminescent yield, so that they will not be very influential in the kind of measurement described above. In addition, the method of establishing the albedo reference level noted hereinbefore will greatly suppress the effect of these phosphorescent species because they will hardly have had time to appreciably decay between the signal and albedo measurements.

Figure 10:
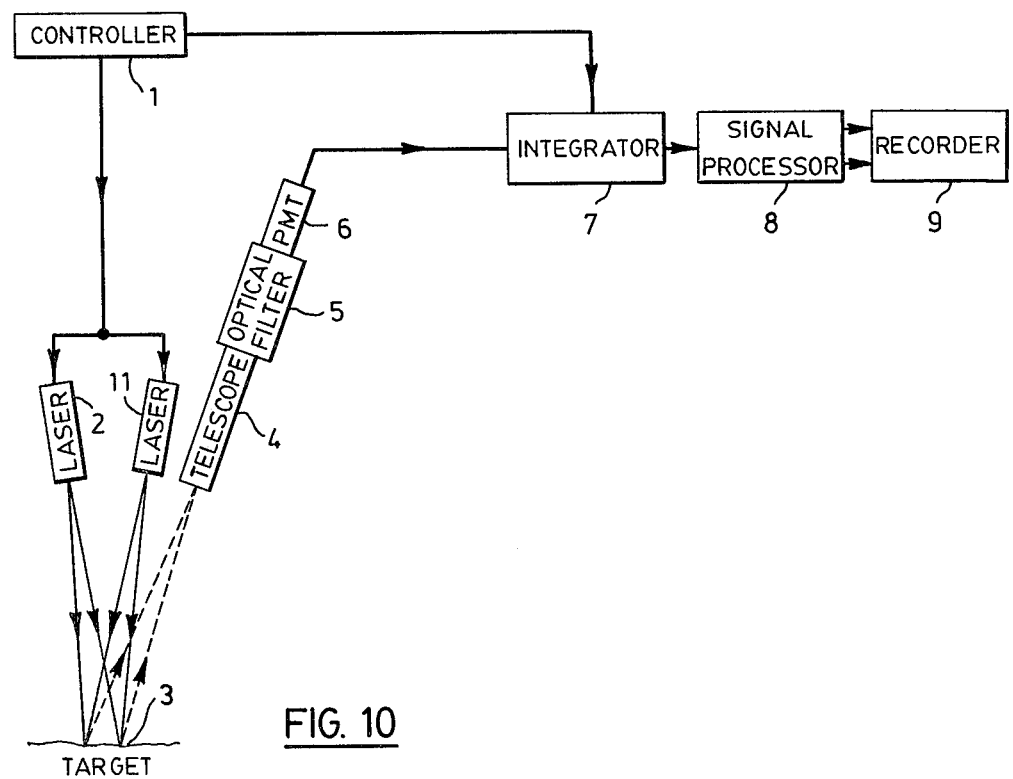
FIG. 10 is a block diagram of typical, multichannel excitation equipment which may be used in the practice of this invention.

An additional means of discriminating between different photoluminescent species is to employ excitation radiation sources of different wavelengths, e.g., a nitrogen laser of 337 nm in wavelength and an excimer laser of 250 nm wavelength. Some luminescent species will not be highly excited by the former, e.g., calcite and scheelite. In order to utilize this variation of photoluminescent response with excitation frequency, the apparatus of FIG. 10 might be employed. FIG. 10 is similar to FIG. 7 except that two pulsed laser sources 2 and 11 producing radiation at significantly different wavelengths are pulsed sequentially by the controller 1 to produce differing levels of luminescence in different species. The controller 1 then synchronously gates the integrator 7 to produce photoluminescent decay information for each laser separately. Diagnostic information leading to the resolution of differing luminescent species may be obtained by a later comparison of these decay curves.

Whereas FIG. 10 has been shown for two lasers and a single spectral channel, it is obvious that more than 2 lasers and more than 1 spectral channel, as in FIG. 9, may be employed for additional resolution of different photoluminescent species.

The foregoing discussion has centered on the use of a short duration pulse of radiation as the exciting source for the photoluminescence, and the measurement of the time and spectral characteristics of the light emitted from the photoluminescent materials after the interruption of the incident pulse. Because of the long lifetime characteristic of photoluminescence of minerals of interest, such measurements may be used to detect such minerals in the presence of the multitude of other short lifetime luminescent materials.

More generally, however, the same characteristic of long lifetime may be employed using many other time varying sources of incident radiation. The short duration pulse which has been discussed previously may be considered to be an approximation to an "impulse function". This is one fundamental waveform. Another is the sine wave of angular frequency $\omega$. Any periodic function may be represented as a sum of sine waves of different frequencies.

Figure 11:
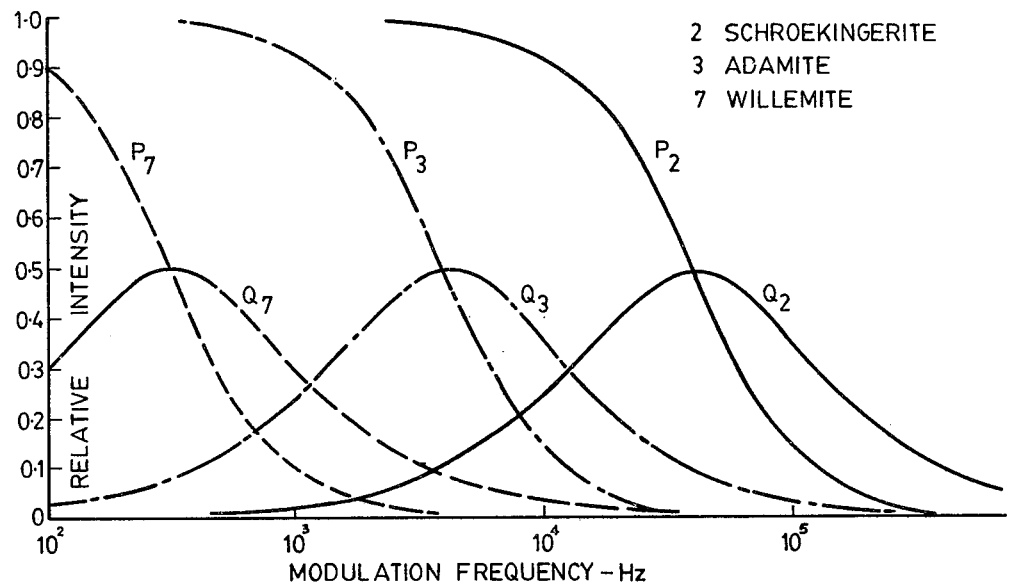
FIG. 11 shows the variation of the photoluminescence of adamite, schroekingerite and willemite with the frequency of modulation of the incident light.

The effect of a long lifetime of photoluminescence, when a sine wave modulated excitation is employed, is to produce a sine wave photoluminescence which has a time or phase lag relative to the exciting waveform and an amplitude which decreases as the frequency of modulation is increased. FIG. 11 shows the variation with modulation frequency of the in-phase and quadrature components of photoluminescence of some of the same minerals as are noted in FIG. 2. All responses have been normalized to unity with respect to the in-phase photoluminescence at very low frequency.

It will be noted that the in-phase response for each material progressively decreases as the modulation frequency is increased. The quadrature response, however, initially rises with increasing frequency, reaches a maximum and then drops progressively thereafter as the frequency continues to rise. The frequency $f_m$ at which the quadrature response is a maximum is a useful one, for if it is known for a particular mineral, then it may be used to maximize the detectability of that mineral.

In fact, if the photoluminescent decay has the form of equation (1) with a lifetime $\tau$, it may be shown by means of a Fourier Transform that $$f_m = \frac{1}{2\pi\tau} \quad (2)$$

For example,
if $\tau = 10^{-5}$ seconds, $f_m = 16$ kHz and
if $\tau = 10^{-4}$ seconds, $f_m = 1600$ Hz For our purposes the frequency range of modulation from about 3 kHz to about 160 kHz will be of interest. It should be pointed out also that a measurement of the phase lag of photoluminescence relative to the phase of the modulation waveform is an alternate means of detection of the presence of a quadrature component, although the measurement of the quadrature component directly is to be preferred.

Figure 12:
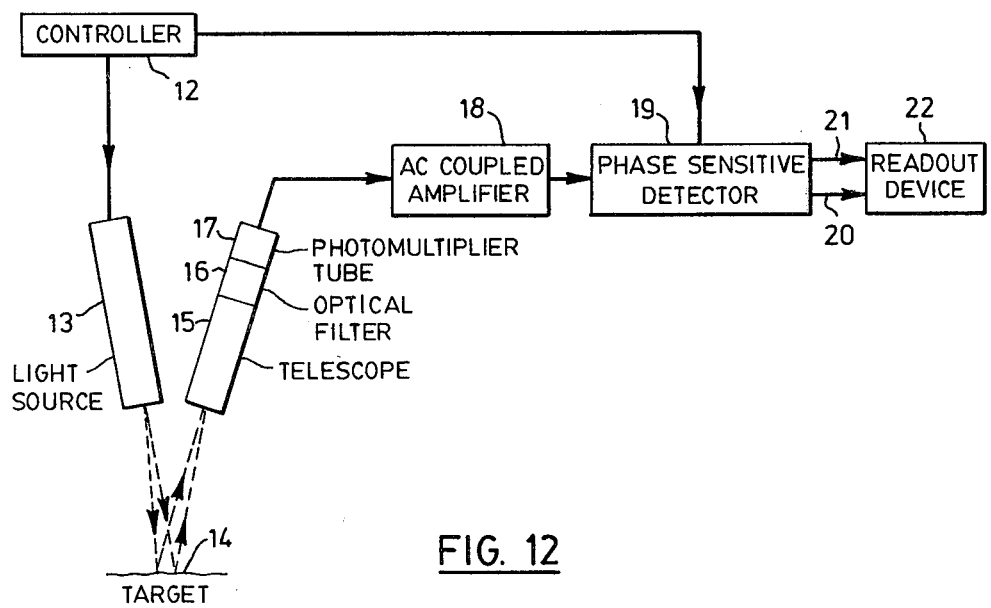
FIG. 12 is a block diagram showing further equipment which may be used in practising the instant invention.

To utilize this approach in a practical embodiment of this invention, apparatus of the type shown in FIG. 12 may be used. In this embodiment the electronic controller 12 modulates the output of the UV light source 13 in accordance with a sine wave of selected frequency, the output of the source being directed towards the ground target 14. The source may be, for example, a helium-cadmium laser with a strong line at 325 nm wave length, or other suitable modulatable UV light source. The telescope 15 is focused on the same target. The output of the telescope is passed through an optical filter 16 whose pass band encompasses the spectral peak of the photoluminescence from the mineral desired. The filtered beam then enters a low noise photomultiplier tube 17 which has optimum efficiency in the desired region of the spectrum. The electrical output of the PMT is amplified in an AC coupled amplifier 18 in order that the steady albedo level and PMT dark current will be largely rejected. The output of this amplifier then passes to a phase sensitive detector 19 the phase reference for which is provided by controller 12.

The phase sensitive detector performs two functions:

(a) It acts as a very narrow band filter, passing only those signals with the frequency of the light source. A marked improvement in signal/noise ratio is thereby obtained.

(b) It separates the incoming signal into the in-phase 20 and quadrature 21 components using the phase reference of the modulation signal provided by controller 12.

The outputs 20 and 21 of phase sensitive detector 19 are fed to a readout device 22, which may include digital indicators or a two channel graphic or digital recorder, etc., as required by the application at hand. Of these two outputs the quadrature component is the most informative as it provides a time resolved measurement which is sensitive to photoluminescence of long lifetime, the preferred lifetime being selected by the proper choice of the modulation frequency employed. As may be seen from FIG. 11, if, for example, the frequency is selected so as to be optimum for photoluminescences with a 50 microsecond lifetime (i.e., about 4 kHz), the quadrature response from shortlived species, e.g., 1 microsecond or less, will be reduced to less than 4% of the maximum value. The in-phase channel will be responsive to all photoluminescent materials with lifetimes less than a certain value determined by the modulation frequency employed. As such, it will not provide as much useful information as the quadrature channel.

Whereas it has been suggested in connection with FIG. 12 that a specific modulation frequency is used, it is obvious that more than one modulation frequency may be employed, either consecutively or concurrently, to obtain information about luminescent species with different lifetimes. If concurrent frequencies are employed, this signifies that the resultant modulation waveform will look non-sinusoidal, e.g., a square wave or saw tooth wave, etc. Resolution of the individual in-phase and quadrature components then would be accomplished by the use of a multiplicity of phase detectors, each operating at a different frequency. The phase reference for each detector still would be provided from the controller. If more than one modulation frequency is employed, an alternative diagnostic criterion for the presence of luminescent species with desired lifetime would be the change with frequency of the in-phase or total luminescence.

In addition, whereas a single optical filter and PMT are shown in FIG. 12, it is obvious that the light collected by the telescope may be split by a beam splitter and then passed through a series of different optical filters, as in FIG. 9, whereby to obtain information about the in-phase and quadrature components of the photoluminescent response of the ground separately in different spectral bands properly spaced across the desired spectrum.

Referring again to the embodiment of FIG. 12, we have found that it is possible to modulate certain mercury lamps (e.g. Ultraviolet Products Inc., Type 22 SCS) by 100% to about 30 kHz and better than 70% up to 200 kHz. These can provide very good UV light sources 13, with a strong line at 253.7 nm. By using suitable phosphor coatings on such lamps, it is possible to convert them into longer wave UV modulatable light sources, for those minerals (e.g., fluorite) whose luminescence is preferentially excited by such longer wave lengths.

Figure 13:
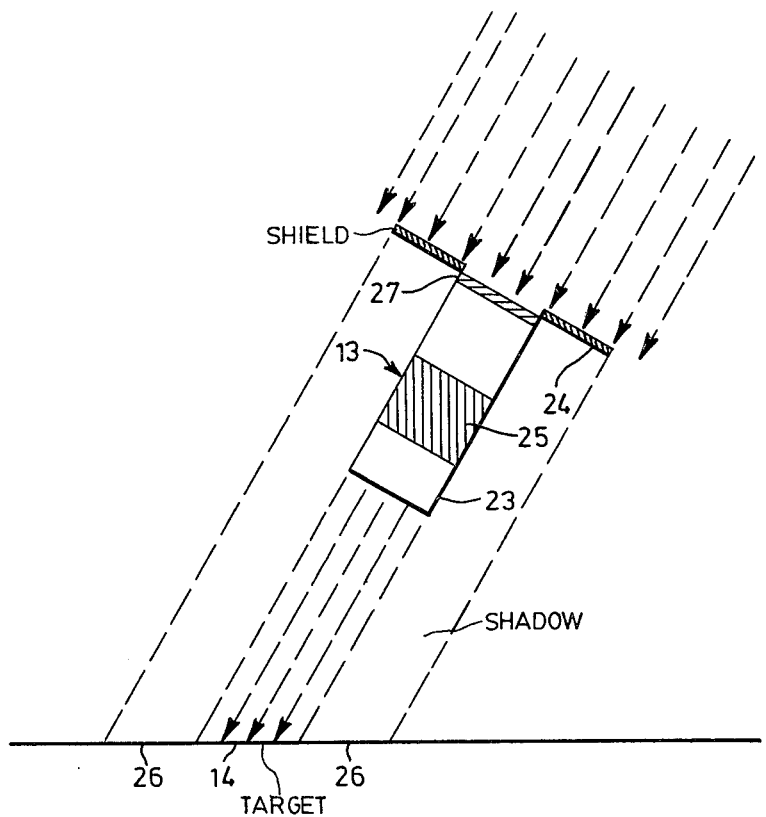
FIG. 13 is a block diagram illustrating other equipment which may be used in practising the instant invention.

Sunlight itself contains a substantial UV component down to about 300 nm wave length. Under bright sunlit conditions, this can be used as the UV light source 13 in the embodiment shown in FIG. 13. A cylindrical tube 23 is orientable to be parallel to the incident sunlight. A shield 24 concentric with the cylinder provides a region of shadow about the tube. There is a modulation means 25, which is driven by the electronic controller 12, which modulates the intensity of the sunlight which is allowed to pass through this tube and illuminate the target 14. This modulation means 25 may be an electro-optical device (e.g., Pockels) using, for example, KDP (potassium dihydrogen phosphate) or an electromechanical rotating shutter. The telescope 15 is focused on the illuminated target 14, which, in this instance is surrounded by a shadow area 26, thus cutting down on the amount of scattered sunlight likely to be seen by the telescope.

An optical filter 27 is placed at the entrance to the tube 23 in order to allow only the UV rays, which are desirable for luminescent excitation to pass through to the target. This further cuts down on the level of reflected light, in the spectral region of interest for detection of luminescent minerals in this invention, which may enter the telescope.

In this fashion, instead of strong sunlight being a major source of background noise, it may be utilized as a "free" source of modulatable light for certain applications of this invention.

Sunlight reflected from materials at the earth's surface contains wavelengths throughout the spectral regions of interest for peak emission from the luminescing minerals, the detection of which is the object of this invention. For this reason, sunlight may cause a high background light level or albedo and therefore make it difficult to detect small changes in light level due to luminescence. One way of circumventing this is to use an excitation light source which is sufficiently intense to override the albedo, but this is limited by practical and safety considerations. Another way is to use nocturnal detection. Still a third way is to take advantage of the Fraunhofer lines which appear in the sunlight spectrum.

Fraunhofer line detection has been employed by some workers in the detection of steady state, solar excited luminescence (e.g., see "Use of an Airborne Fraunhofer Line Discrimination for the detection of Solar Stimulated Luminescence" by R. D. Watson et al., U.S.G.S. Open File Report 76202), but this approach has no ability to resolve different photoluminescent minerals by virtue of the differing lifetimes which is an essential part of this invention.

Figure 14:
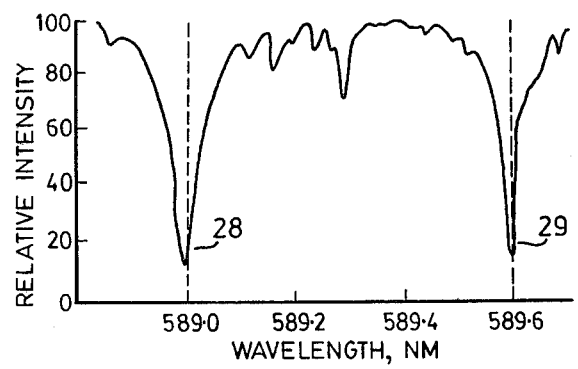
FIG. 14 shows the Fraunhofer absorption lines in a portion of the sunlight spectrum.

FIG. 14 shows a section of the sunlight spectrum between 588.8 nm and 589.8 nm. The peak general intensity level over this region is shown as 100% (arbitrary units). Two sharp gaps (28 and 29) can be seen, at 589.0 and 589.6 nm, where the relative intensity is reduced to less than 15%. These are typical Fraunhofer absorption lines due to absorption of the sun's radiation by relatively cool gases in the sun's outer atmosphere. The width of these lines ranges from less than 0.01 nm to 0.5 nm or more, and the central intensity of some lines is less than 10% of the adjacent continuum.

There are many of these Fraunhofer lines, irregularly spaced throughout the near UV, visible and near IR regions of the electromagnetic spectrum. There are, for example, broad and deep calcium lines at 386.8 and 393.4 nm, a hydrogen line at 434.0 and other lines at 486.1 nm, 589.0 nm and 656.3 nm, etc.

It is possible to employ narrow band optical filters (e.g., Fabry Perot etalon filter) with a half-width of less than 0.1 nm and a peak transmission of more than 50%. The centre wavelength of the filter may be tuned by a precision thermostat control to the centre of a Fraunhofer line, so that only spectral energy which lies primarily within that Fraunhofer line is passed. When the Fraunhofer line selected lies in the vicinity of a luminescence emission peak of a mineral of interest in this invention, then it is easy to see that the ratio of luminescence/albedo energy (or signal/noise) for that mineral can be considerably increased, possibly by a factor of up to 4, for daylight operation. This is true even though the signal strength is itself reduced greatly by the filter, so long as the residual signal level is above the electronic detection noise of the system.

The 486.1 nm line, for example, falls close to a principal emission peak of hydrozincite (FIG. 5). Simultaneous operation at more than one Fraunhofer wavelength will permit multi-spectral analysis of luminescence and will, therefore, contribute to the detection and identification of a variety of different luminescent minerals.

An important feature of the instant invention that can be observed from Table 1 is that the lifetimes of photoluminescence of the minerals of zinc, tungsten, molybdenum, fluorine and mercury listed therein all are between 1 and 50 microseconds, making detection of these minerals possible by observations within this time period or, equivalently, by use of modulation frequencies of between about 3 kHz and 160 kHz (obtainable from equation (2). This enables selective detection of the economically important minerals of fluorine and mercury, although these last two are less economically significant and have relatively low fluorescent yields.

The taking of observations in the 1–50 mocrosecond time frame (or the use of modulation frequencies of from about 3 kHz to about 160 kHz) provides a technique for maximizing the detection of minerals of zinc, tungsten, molybdenum, fluorine and mercury. Of the many uranyl minerals, only zippeite and andersonite exhibit lifetime of less than 50 microseconds. Since both of these minerals are rarely observed at the surface of the earth, the present method will not be optimum for the detection of uranium minerals which do occur at the surface. Of course there exist adequate remote sensing techniques, based on gamma radiometric measurements, for surface uranium occurrences.

TABLE 1
LUMINESCENT PROPERTIES OF SOME MINERALS OF ECONOMIC INTEREST

| NAME | | LIFETIME Microseconds | EMISSION PEAK λ - nm |
|---|---|---|---|
| Adamite | $Zn_2(OH)AsO_4$ | 50 | 510 |
| Autunite | $Ca(UO_2)_2(PO_4)_2 \cdot 10H_2O$ | 60 | 525 |
| Cinnabar | HgS | 11 | 520 |
| Ferberite | $FeWO_4$ | 4 | 465 |
| Fluorite | $CaF_2$ | 2 | 420 |
| Hydrozincite | $Zn_5(OH)_6(CO_3)_2$ | 1 | 455 |
| Powellite | $Ca(Mo,W)O_4$ | 30 | 570 |
| Scheelite | $CaWO_4$ | 9 | 405 |
| Schroekingerite | $(NaCa_3(UO_2)(CO_3)_3SO_4F \cdot 10H_2O$ | 125 | 505 |
| Willemite | $Zn_2SiO_4$ | 400 | 520 |
| Zippeite | $UO_3 \cdot SO_3 \cdot nH_2O$ | 3 | 540 |
| Andersonite | $Na_2Ca(UO_2)(CO_3)_3 \cdot 6H_2O$ | 150 | 500 |
| Anglesite | $PbSO_4$ | 215 | 475 |
| Cerussite | $PbCO_3$ | 218 | 475 |

TABLE 2

| Mineral/Origin | Colour of Fluorescence | Lifetime (μs) |
|---|---|---|
| Miscellaneous Samples | | |
| Marble, Beaver City, Utah | Blue | <0.2 |
| Marble, Nevada | Blue-White | <0.2 |
| Granodiorite, Nevada | Orange | <0.2 |
| Amphibolite, Unknown | Blue | <0.2 |
| Quartz-monozonite, Nevada | Pink | <0.2 |
| Amphibole-gneiss, Nevada | Blue | <0.2 |
| Gossan, Nevada | Blue | <0.2 |
| Barite, Unknown | Green | <0.2 |
| Hornblende, Unknown | Blue | <0.2 |
| Quartzite iron-stained, Unknown | Blue | <0.2 |
| Marble, Stoklosa Ont. | Blue | <0.2 |
| Limestone, Nevada | — | <0.2 |
| Breccia, Smoke Valley, Nevada | — | <0.2 |
| Gneiss, Ontario | Red/Blue | <0.2 |
| Phyllite, Ontario | Red/Blue | <0.2 |
| Syerite, Ontario | Red/Blue | <0.2 |
| Schist, Nevada | Blue | <0.2 |
| Quartz weathered, Smoky Valley, Nevada | Red | <0.2 |
| Amber tourmeline, Ont. | Red-Orange | <0.2 |
| Calcite, Frontenac Twp., Ont. | Red-Orange | <0.2 |
| Mineral set - Ontario Department of Mines | | |
| 'Limonite' | Blue | <0.5 |
| 'Siderite' | Red | <0.5 |
| 'Spodumene' | White | <0.1 |
| 'Quartz' | Blue | <0.2 |
| 'Feldspar' | Red/Blue | <0.2 |
| 'Nepheline' | White/Violet | 0.16 |
| 'Pyroxene' | Red/Blue | <0.5 |
| 'Mica' | White | 0.2 |
| 'Barite' | White | <0.2 |
| 'Garnet' | Blue | <0.2 |
| 'Kyanite' | Blue | <0.2 |
| 'Graphite' | Blue | <0.5 |
| 'Talc' | Blue-White | <0.2 |
| 'Serpentine' | Blue | <0.2 |
| 'Gypsum' | Blue | <0.2 |
| 'Halite' | Blue-White | <0.2 |
| 'Granite' | Red | <0.5 |
| 'Syenite' | Red/Violet | <0.2 |
| 'Diorite' | Blue | <0.2 |
| 'Gabbro' | Blue | <0.2 |
| 'Diabase' | Blue | <0.1 |
| 'Porphyry' | Blue | <0.5 |
| 'Rhyolite' | Blue-White | <0.5 |
| 'Basalt' | Blue | <0.5 |
| 'Amygdaloidal Basalt' | Blue | <0.2 |
| 'Conglomerate' | Blue/Red | <0.1 |
| 'Greywacke' | Blue | <0.5 |
| 'Sandstone' | Blue/White | <0.5 |
| 'Shale' | Blue | <0.1 |
| 'Limestone' | Blue | <0.1 |

TABLE 2-continued

| Mineral/Origin | Colour of Fluorescence | Lifetime (μs) |
|---|---|---|
| 'Dolomite' | Blue-White | <0.1 |
| 'Chert' | Blue | <0.1 |
| 'Iron Formation' | Blue | <0.5 |
| 'Lignite' | Blue | <0.5 |
| 'Slate' | Blue | <0.5 |
| 'Crystalline Limestone' | Blue | <0.1 |
| 'Gneiss' | | <0.1 |
| weaker component | | |
| 'Schist' | Blue/Violet | <0.5 |

What we claim is:

1. A method of selectively rejecting the fluorescent response of the abundant photoluminescent rocks and substances which may occur at the surface of the earth, while detecting the fluorescent response of a non-uranyl mineral of economic significance selected from the group consisting of minerals of zinc, fluorine, tungsten, molybdenum, mercury and other elements having lifetimes of photoluminescence between 1 and 50 microseconds through consideration of their differences in photoluminescent lifetimes; said method comprising the steps of directing at the ground electromagnetic radiation having an intensity that varies with time and of a wavelength that causes photoluminescence of said mineral; selectively detecting photoluminescent emission from said mineral in a wavelength region which is characteristic of emission of photoluminescence of said mineral; and selectively detecting the presence of said mineral by measuring the time varying detected photoluminescence excited by said radiation and due to minerals selected from said group and having lifetimes of photoluminescence between 1 and 50 microseconds.

2. A method as claimed in claim 1 wherein said electromagnetic radiation is in the form of a pulse and said time varying detected luminescence is measured by measuring transient decay of said detected photoluminescence after detection of the onset of said photoluminescent emission and starting at a time equal to the sum of (a) the time duration of said pulse and (b) between 1 and 50 microseconds.

3. A method as claimed in claim 1 wherein said electromagnetic radiation is modulated with a fundamental frequency of modulation between about 3 kHz and about 160 kHz and said time varying detected photoluminescence is measured by measuring the phase lag thereof relative to the phase of said modulation of said electromagnetic radiation.

4. A method as claimed in claim 1 wherein said electromagnetic radiation is modulated with a fundamental frequency of modulation between about 3 kHz and about 160 kHz, said time varying detected photoluminescence is separated into in-phase and quadrature components relative to the phase of said modulation of said electromagnetic radiation, and said time varying detected luminescence is measured by measuring said quadrature component.

5. A method according to any one of claims 1, 2, 3 or 4, wherein said mineral is hydrozincite.

6. A method according to any one of claims 1, 2, 3 or 4, wherein said mineral is scheelite.

7. A method according to any one of claims 1, 2, 3 or 4, wherein said mineral is powellite.

8. A method according to any one of claims 1, 2, 3 or 4, wherein said mineral is cinnabar.

9. A method according to any one of claims 1, 2, 3, or 4, wherein said mineral is fluorite.

10. A method according to any one of claims 1, 2, 3 or 4, wherein said mineral is ferberite.

11. A method according to any one of claims 1, 2, 3 or 4, wherein said mineral is adamite.

12. A method as claimed in claim 1 wherein said wavelength is centered on a Fraunhofer solar absorption line close to the characteristic wavelength of photoluminescence of said mineral.

13. A method as claimed in claim 1 wherein said electromagnetic radiation is solar radiation.

14. A method of selectively rejecting the fluorescent response of the abundant photoluminescent rocks and substances which may occur at the surface of the earth, while detecting the fluorescent response of certain non-uranyl minerals of economic significance selected from the group consisting of minerals of zinc, fluorine, tungsten, molybdenum, mercury and other elements having lifetimes between 1 and 50 microseconds through consideration of their differences in photoluminescent lifetimes; said method comprising the steps of directing at the ground electromagnetic radiation having an intensity that varies with time and of a wavelength that causes photoluminescence of said minerals; selectively detecting photoluminescent emissions from said minerals in at least one wavelength region which is characteristic of emission of photoluminescence of said minerals; and selectively detecting the presence of said minerals by measuring the time varying detected photoluminescence excited by said radiation and due to minerals selected from said group and having lifetimes of photoluminescence between 1 and 50 microseconds.

15. A method as claimed in claim 14 wherein said minerals the presence of which is being detected have different characteristic wavelengths of photoluminescence when irradiated by said electromagnetic radiation and wherein said photoluminescent emissions from said minerals are selectively detected in different wavelength regions which are characteristic of photoluminescence of said minerals.

16. A method as claimed in claim 14 wherein said electromagnetic radiation is modulated with at least two different frequencies of modulation between about 3 kHz and about 160 kHz and said time varying detected photoluminescence is measured by measuring the phase lag thereof relative to the phase of said modulation of said electromagnetic radiation for each of said frequencies.

17. A method as claimed in claim 16 wherein said minerals the presence of which is being detected have different characteristic wavelengths of photoluminescence when irradiated by said electromagnetic radiation and wherein said photoluminescent emissions from said minerals are selectively detected in different wavelength regions which are characteristic of photoluminescence of said minerals.

18. A method as claimed in claim 14 wherein said electromagnetic radiation is modulated with at least two different frequencies of modulation between about 3 kHz and about 160 kHz, said time varying detected luminescence is separated into in-phase and quadrature components relative to the respective phases of said modulation of said electromagnetic radiation, and said time varying detected luminescence is measured by measuring said quadrature components.

19. A method as claimed in claim 18 wherein said minerals the presence of which is being detected have different characteristic wavelengths of photoluminescence when irradiated by said electromagnetic radiation and wherein said photoluminescent emissions from said minerals are selectively detected in different wavelength regions which are characteristic of photoluminescence of said minerals.

20. A method as claimed in claim 14 wherein said electromagnetic radiation is modulated with at least two different frequencies of modulation between about 3 kHz and about 160 kHz and said time varying detected photoluminescence is measured by measuring the amplitude of said detected photoluminescence responsive to said electromagnetic radiation at said different frequencies of modulation.

21. A method as claimed in claim 20 wherein said minerals the presence of which is being detected have different characteristic wavelengths of photoluminescence when irradiated by said electromagnetic radiation and wherein said photoluminescent emissions from said minerals are selectively detected in different wavelength regions which are characteristic of photoluminescence of said minerals.

22. A method as claimed in claim 14 wherein said electromagnetic radiation is obtained from at least two light sources of substantially different wavelengths and is sequentially directed at the ground.

23. Apparatus for selectively rejecting the fluorescent response of the abundant photoluminescent rocks and substances which may occur at the surface of the earth, while detecting the fluorescent response of a non-uranyl mineral of economic significance selected from the group consisting of minerals of zinc, fluorine, tungsten, molybdenum, mercury and other elements having a lifetime of photoluminescence between 1 and 50 microseconds through consideration of their differences in photoluminescent lifetimes; said apparatus comprising a source of electromagnetic radiation having a wavelength that causes photoluminescence of said mineral; means for modulating said source with a fundamental frequency of modulation between about 3 kHz and about 160 kHz; means for selectively detecting photoluminescent emission from said mineral in a wavelength region which is characteristic of emission of photoluminescence of said mineral; and means for measuring the phase lag of the detected photoluminescent emission from said mineral relative to the phase of said modulation of said electromagnetic radiation.

24. Apparatus according to claim 23 wherein said source of electromagnetic radiation is solar radiation.

25. Apparatus according to claim 24 wherein said means for selectively detecting includes optical filter means centered on a Fraunhofer absorption line close to a characteristic wavelength of photoluminescence of said mineral.

26. Apparatus for selectively rejecting the fluorescent response of the abundant photoluminescent rocks and substances which may occur at the surface of the earth, while detecting the fluorescent response of a non-uranyl mineral of economic significance selected from the group consisting of minerals of zinc, fluorine, tungsten, molybdenum, mercury and other elements having a lifetime of photoluminescence between 1 and 50 microseconds through consideration of their differences in photoluminescent lifetimes; said apparatus comprising a source of electromagnetic radiation having a wavelength that causes photoluminescence of said mineral; means for modulating said source with a fundamental frequency of modulation between about 3 kHz and about 160 kHz; means for selectively detecting photoluminescent emission from said mineral in a wavelength region which is characteristic of emission of photoluminescence of said mineral; means for separating the detected photoluminescent emission into in-phase and quadrature components relative to the phase of said modulation of said electromagnetic radiation, and means for measuring said quadrature component.

* * * * *